(12) United States Patent
Shah et al.

(10) Patent No.: US 10,034,865 B2
(45) Date of Patent: Jul. 31, 2018

(54) SURFACTANT-FREE HIV PROTEASE INHIBITOR COMPOSITION AND METHOD OF MANUFACTURING THEREOF

(71) Applicant: Kashiv Pharma, LLC, Bridgewater, NJ (US)

(72) Inventors: Navnit H. Shah, Clifton, NJ (US); Atsawin Thongsukmak, Piscataway, NJ (US); Jaydeep Vaghashiya, Woodbridge, NJ (US); Dipen Desai, Whippany, NJ (US); Wantanee Phuapradit, Montville, NJ (US)

(73) Assignee: Kashiv Pharma, LLC, Bridgewater, NJ (US)

( * ) Notice: Subject to any disclaimer, the term of this patent is extended or adjusted under 35 U.S.C. 154(b) by 0 days.

(21) Appl. No.: 15/001,960

(22) Filed: Jan. 20, 2016

(65) Prior Publication Data

US 2017/0071915 A1     Mar. 16, 2017

Related U.S. Application Data

(60) Provisional application No. 62/216,566, filed on Sep. 10, 2015.

(51) Int. Cl.
| | |
|---|---|
| *A61K 31/427* | (2006.01) |
| *A61K 47/02* | (2006.01) |
| *A61K 9/20* | (2006.01) |
| *A61K 47/32* | (2006.01) |

(52) U.S. Cl.
CPC .......... *A61K 31/427* (2013.01); *A61K 9/2009* (2013.01); *A61K 9/2027* (2013.01); *A61K 9/2095* (2013.01); *A61K 47/02* (2013.01); *A61K 47/32* (2013.01)

(58) Field of Classification Search
CPC .. A61K 9/2009; A61K 9/2027; A61K 9/2095; A61K 31/427; A61K 47/02; A61K 47/32
See application file for complete search history.

(56) References Cited

U.S. PATENT DOCUMENTS

| | | | |
|---|---|---|---|
| 6,599,528 B1 | 7/2003 | Rosenberg et al. | |
| 8,268,349 B2 | 9/2012 | Rosenberg et al. | |
| 8,377,952 B2 | 2/2013 | Rosenberg et al. | |
| 8,399,015 B2 | 3/2013 | Rosenberg et al. | |
| 2014/0234415 A1* | 8/2014 | McDermott ....... | A61K 31/7068 424/465 |
| 2015/0045400 A1 | 2/2015 | Parthasaradhi et al. | |
| 2015/0111909 A1* | 4/2015 | Meergans ............ | A61K 31/427 514/274 |

FOREIGN PATENT DOCUMENTS

| | | |
|---|---|---|
| CN | 1695621 A | 11/2005 |
| IN | 2115/CHE/2012 | * 11/2013 |
| WO | 2011/141192 A1 | 11/2011 |

OTHER PUBLICATIONS

Djuric, D. Continuous Granulation with a Twin-Screw Extruder, Dissertaion, 2008.*
Karl et al. Suitability of Pure and Plasticized Polymers for Hot Melt Extrusion, BASF, 2010.*
Alonzo et al., "Understanding the behaviour of amorphous pharmaceutical system during dissolution", Pharmaceutical Research, vol. 27, No. 4, Apr. 2010, pp. 608-618.
Dias L., et al., "Physical and Oral Dog Bioavailability Evaluation of ABT-538:PVP Co-precipitates, PDD 7475" in: Pharmaceutical Research, vol. 13 (9), Vincent H.L. Lee., et al., eds., Plenum Press, 1996, pp. S-351.
Frank et al., "The amorphous solid dispersion of the poorly soluble ABT-102 forms nano/microparticulate structures in aqueous medium: impact on solubility", International Journal of Nanomedicine, Nov. 9, 2012, pp. 5757-5768.
Garren et al., "Bioavailability of generic ritonavir and liponavir/ritonavir tablet products in a dog model", Abbott Laboratories, Journal of Pharmaceutical Sciences, Final Publication Feb. 19, 2009, 6 pages.
Klein et al., "The effect of food on ritonavir bioavailability following administration of ritonavir 100 mg film-coated tablet in healthy adult subjects", Abbott Laboratories, Copyright Abbott 2008, 4 pages.
Martin D., et al., "Method of Preparing an Orally Bioavailable Solid Formulation of an Insoluble Protease Inhibitor as a Coprecipitate with PVP and Other Excipients, PDD 7474" in: Pharmaceutical Research, vol. 13 (9), Vincent H.L. Lee., et al., eds., Plenum Press, 1996, pp. S-351.
Sun et al., "Stability of amorphous pharmaceutical solids: Crystal growth mechanisms and effect of polymer additives", The AAPS Journal, vol. 14, No. 3, Sep. 2012, pp. 380-388.
International Search Report for PCT/US2016/050517, dated Nov. 15, 2016, 3 pages.

* cited by examiner

*Primary Examiner* — Johann R Richter
*Assistant Examiner* — Genevieve S Alley
(74) *Attorney, Agent, or Firm* — Lerner, David, Littenberg, Krumholz & Mentlik, LLP

(57) ABSTRACT

Disclosed are pharmaceutical compositions, e.g., in the form of tablets, containing a therapeutically effective amount of an HIV protease inhibitor, e.g., ritonavir, a pharmaceutically acceptable aqueous-soluble polymer, and an erosion-enhancing agent having a particle size distribution in the range of about 1 μm to about 350 μm, wherein the composition is substantially free or free of surfactant. Methods of making the compositions, and methods of using them to treat HIV infection are also provided.

36 Claims, 5 Drawing Sheets

SURFACTANT-FREE HIV PROTEASE INHIBITOR COMPOSITION AND METHOD OF MANUFACTURING THEREOF

CROSS-REFERENCE TO RELATED APPLICATION

The present application claims the benefit of the filing date of U.S. Provisional Patent Application No. 62/216,566 filed Sep. 10, 2015, the disclosure of which is hereby incorporated herein by reference.

BACKGROUND OF THE INVENTION

Bioavailability is used as a measure of potential efficacy for an orally administered drug. Various factors can affect the bioavailability of orally administered dosage forms. These factors include aqueous solubility, drug absorption, dosage strength, and first pass effect. Aqueous solubility is generally regarded as the main factor that affects bioavailability of HIV protease inhibitors.

Protease inhibitors inhibit cleavage of a protein into peptides. Inhibition of HIV protease is an important approach for the therapeutic intervention in HIV infection. Since the 1990s, these drugs have been a key component of anti-retroviral therapies for HIV/AIDS. One such example of an HIV protease inhibitor is ritonavir.

The state of the art indicates that in order to achieve therapeutically acceptable bioavailability of HIV protease inhibitors, they must be formulated with surfactants; that is, surfactants are critical to achieve therapeutic levels of bioavailability. For example, U.S. Pat. No. 6,599,528 describes a mechanically stable pharmaceutical composition that comprises one or more melt-processable polymers and more than 10% by weight surfactant or a "surface-active substance" in addition to one or more active ingredients that include protease inhibitors. The patent teaches that the improvement in processability is desired when larger amounts of surface-active substances in the range of more than 10% by weight are needed to effectively solubilize the active ingredient.

U.S. Pat. No. 8,399,015 teaches a solid pharmaceutical dosage form comprising a solid dispersion that includes an HIV protease inhibitor (e.g., ritonavir and lopinavir), a pharmaceutically acceptable aqueous-soluble polymer, and a pharmaceutically acceptable surfactant having a hydrophilic-lipophilic balance (HLB) value of from 4 to 10. According to the patent, the inclusion of a surfactant having an HLB value of from 4 to 10 is essential for markedly improving the bioavailability of the HIV protease inhibitor.

U.S. Pat. No. 8,268,349 teaches a solid pharmaceutical dosage form comprising a solid dispersion containing sorbitan monolaurate, at least one pharmaceutically acceptable aqueous-soluble polymer, colloidal silica, and ritonavir.

SUMMARY OF THE INVENTION

The present invention is based on the discovery that therapeutically effective amounts of ritonavir can be formulated for oral administration without using a surfactant. As shown in the working examples and figures herein, compositions of the present invention, which do not contain a surfactant but rather an erosion-enhancing agent, surprisingly exhibit comparable stability and bioavailability when compared with known dosage forms of HIV protease inhibitors that do contain a surfactant, such as the commercially available dosage form of ritonavir known as NORVIR®.

A first aspect of the present invention is directed to a pharmaceutical composition containing a therapeutically effective amount of an HIV protease inhibitor, a pharmaceutically acceptable aqueous-soluble polymer, and an erosion-enhancing agent having a particle size distribution in the range of about 1 μm to about 350 μm, wherein the composition is substantially free of surfactant. The HIV protease inhibitor is dispersed in the composition as an amorphous (i.e., noncrystalline) solid. In some embodiments, the HIV protease inhibitor is ritonavir. In some embodiments, the compositions are totally free of surfactant. The composition may include additional pharmaceutically acceptable excipients, such as lubricants and glidants. For ease of oral administration, the composition may be formulated as tablets. The compressed tablets thus formed may be film coated for aesthetic and handling purposes.

A second aspect of the present invention is directed to a method of making the pharmaceutical composition, comprising formulating a therapeutically effective amount of an HIV protease inhibitor, a pharmaceutically acceptable aqueous-soluble polymer, and an erosion-enhancing agent having a particle size distribution in the range of about 1 μm to about 350 μm, into the pharmaceutical composition, wherein the composition is substantially free of surfactant.

A third aspect of the present invention is directed to a method of treating a subject infected with HIV, comprising administering to said subject a pharmaceutical composition comprising a therapeutically effective amount of an HIV protease inhibitor, a pharmaceutically acceptable aqueous-soluble polymer, and an erosion-enhancing agent having a particle size distribution in the range of about 1 μm to about 350 μm, wherein the composition is substantially free of surfactant.

A fourth aspect of the present invention is directed to the use of a pharmaceutical composition comprising a therapeutically effective amount of an HIV protease inhibitor, a pharmaceutically acceptable aqueous-soluble polymer, and an erosion-enhancing agent having a particle size distribution in the range of about 1 μm to about 350 μm, wherein the composition is substantially free of surfactant as a medicament for the treatment of HIV.

Without intending to be bound by any particular theory of operation, it is believed that the absence of surfactant and presence of an erosion-enhancing agent having the specific particle size distribution disclosed herein contributes to promoting erosion of the formulation and contributes to the dissolution rate so as to maintain the HIV protease inhibitor in a state of super-saturation upon dissolution and when in contact with aqueous fluids in the gastrointestinal tract.

DETAILED DESCRIPTION OF THE INVENTION

Figure 1:
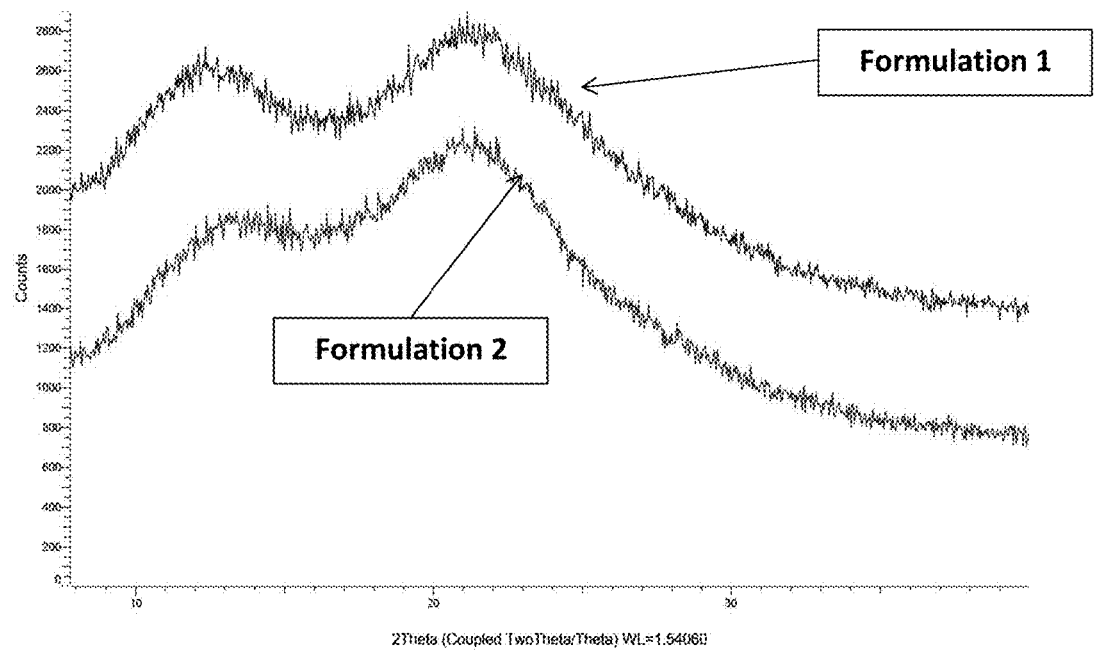
FIG. 1 shows the powder X-ray diffraction pattern for disclosed inventive Formulations 1 and 2, and confirms their amorphous nature, or lack of crystallinity. These results confirm that lack of surfactant, and presence of an amount of aqueous-soluble polymer, have no negative effect on the amorphous nature of the inventive formulation.

HIV protease inhibitors present in the composition of the invention are amorphous and form a stable solid solution with the aqueous-soluble polymer. The term "solid dispersion" as used herein refers to a system in a solid state (as opposed to a liquid or gaseous state) that contains at least two components, wherein one component is dispersed evenly throughout the other component or components. In the specific context of the present invention, the term refers to the HIV protease inhibitor dispersed in a matrix containing a pharmaceutically acceptable aqueous-soluble polymer(s). The term "solid dispersion" thus embraces systems having small particles of one phase dispersed in another phase. When the dispersion of the components is such that the system is chemically and physically uniform or homogeneous throughout or consists of one thermodynamic phase, the dispersion is referred to as a "solid solution" or a "glassy solution". As used herein, a glassy solution is a homogeneous, glassy system in which a solute is dissolved in a glassy solvent.

Examples of HIV protease inhibitors that may be suitable for use in the present invention include ritonavir, lopinavir, saquinavir, nelfinavir, amprenavir, atazanavir, fosamprenavir, tipranavir, darunavir, simeprevir, and indinavir.

The HIV protease inhibitor may be present in the composition in an amount effective for intended therapeutic purposes, e.g., for treating HIV/AIDS.

The HIV protease inhibitor may be present in an amount that generally ranges from about 1 to about 40 wt %, and in some embodiments, about 5 to about 30 wt % based on the total weight of the composition. In terms of absolute amounts, the HIV protease inhibitor may be present in an amount that generally ranges from about 10 mg to about 400 mg, and in some embodiments, from about 25 mg to about 300 mg, e.g., about 100 mg.

The aqueous-soluble polymers employed in the present invention may have a Tg of at least 50° C., and in some embodiments at least 60° C., and in other embodiments from about 80° C. to about 180° C.

Examples of aqueous-soluble polymers that may be suitable for use in the present invention include homopolymers and copolymers of N-vinyl lactams, especially homopolymers and copolymers of N-vinyl pyrrolidone, e.g., polyvinylpyrrolidone (PVP, also known as copovidone), copolymers of N-vinyl pyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate or hydroxypropylmethylcellulose acetate succinate; high molecular polyalkylene oxides such as polyethylene oxide and polypropylene oxide and copolymers of ethylene oxide and propylene oxide, polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, oligo- and polysaccharides such as carrageenans, galactomannans and xanthan gum, or mixtures of one or more thereof.

The aqueous-soluble polymer may be present in the composition in an amount which may prevent or inhibit the HIV protease inhibitor from crystallization. The aqueous-soluble polymer may also assist in the recovery and dissolution stability of the composition. Thus, the aqueous-soluble polymer may be present in an amount that generally ranges from about 20 to about 95 wt %, and in some embodiments from about 35 to about 80 wt %, based on the total weight of the composition.

As used herein, an "erosion-enhancing agent" refers to an ingredient defined as any excipient, small or large molecular structure with any polymorphic form that functions by promoting the erosion of tablet formulation, thus altering the dissolution of the HIV protease inhibitor from the composition once it is exposed to the aqueous fluids in the gastrointestinal tract. Representative examples of erosion-enhancing agents that may be suitable for use in the present invention include anhydrous dicalcium phosphate (EM-COMPRESS®), anhydrous dicalcium phosphate (DI-CAFOS® A 60), anhydrous dicalcium phosphate (DI-CAFOS® A12), sodium chloride, potassium chloride, EUDRAGIT® E PO (i.e., a cationic copolymer based on dimethylaminoethyl methacrylate, butyl methacrylate, and methyl methacrylate), citric acid, tartaric acid, and succinic acid. The particle size of the erosion-enhancing agent generally ranges from about 1 micron to about 350 microns, and in some embodiments from about 1 micron to about 200 microns, and in some embodiments from about 10 microns to about 150 microns. In some embodiments the particle size of the erosion-enhancing agent ranges from about 12 microns to about 150 microns, and in some embodiments is about 12 microns or about 60 microns. The amount of the erosion-enhancing agent generally ranges from about 1 to about 25% w/w, in some embodiments from about 5 to about 20% w/w, and in some embodiments from about 7 to about 15% w/w, based on the total weight of the composition.

For purposes of the present invention, the compositions are substantially surfactant-free, which excludes any functional (e.g., noncontaminating) amount of surfactant, which refers to any amount that contributes to or has an effect on bioavailability of the HIV protease inhibitor. Stated differently, the compositions may in some embodiments contain surfactant in an amount that is functionally negligible. In other embodiments, the compositions are free of surfactant.

The term "surfactant" refers to compounds that lower the surface tension (or interfacial tension) between phases. Surfactants may act as detergents, wetting agents, emulsifiers, foaming agents, and dispersants. Representative examples of surfactants that fall within the term as used herein include saturated and unsaturated polyglycolized glycerides, semisynthetic glycerides, fatty acid esters or ethers of fatty alcohols, polyoxyethylene alkyl ethers, e.g., polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g., polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g., PEG-200 monolaurate, PEG-200 dilaurate, PEG-300 dilaurate, PEG-400 dilaurate, PEG-300 distearate, PEG-300 dioleate; alkylene glycol fatty acid mono esters, e.g., propylene glycol monolaurate (LAUROGLYCOL®); sucrose fatty acid esters, e.g., sucrose monostearate, sucrose distearate, sucrose monolaurate, sucrose dilaurate; or sorbitan fatty acid mono esters such as sorbitan monolaurate (SPAN® 20), sorbitan monooleate, sorbitan monopalmitate (SPAN® 40), or sorbitan stearate, polyoxyethylene castor oil derivates, e.g., polyoxyethyleneglycerol triricinoleate or polyoxyl 35 castor oil (CREMOPHOR® EL; BASF Corp.) or polyoxyethyleneglycerol oxystearate such as polyethylene glycol 40 hydrogenated castor oil (CREMOPHOR® RH 40) or polyethylene glycol 60 hydrogenated castor oil (CREMOPHOR® RH 60); or block copolymers of ethylene oxide and propylene oxide, also known as polyoxyethylene polyoxypropylene block copolymers or polyoxyethylene polypropyleneglycol, such as POLOXAMER® 124, POLOXAMER® 188, POLOXAMER® 237, POLOXAMER® 388, POLOXAMER® 407 (BASF Wyandotte Corp.); or a mono fatty acid ester of polyoxyethylene (20) sorbitan, e.g., polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), and polyoxyethylene (20) sorbitan monolaurate (TWEEN® 20). Examples of surfactants are also disclosed in U.S. Pat. Nos. 8,268,349 and 8,399,015.

The composition may be formulated with one or more pharmaceutical acceptable excipients, representative examples of which include lubricants and glidants.

Representative examples of lubricants that may be suitable for use in the present invention include sodium stearyl fumarate, magnesium stearate, stearic acid, and glyceryl behenate.

The composition may further include a glidant. Representative examples of glidants that may be suitable for use in the present invention include colloidal silica and calcium silicate.

The composition may further include a protective or aesthetic film coat. Such coating compositions may be common ready-to-use coating systems that contain mixtures of polymer, plasticizer, pigments, anti-tacking agents, and opacifiers. Other coatings are also known in the art. Coatings may provide a moisture or oxygen barrier or enhance the aesthetics of the composition, e.g., a tablet composition.

Compositions of the present invention may be prepared in accordance with known techniques. The method of preparation comprises a mixture of at least one HIV protease inhibitor and at least one aqueous-soluble polymer, which is blended for a hot melt extrusion, followed by feeding the mixture into an extruder at a temperature ranging from about 100° C. to about 140° C. to form melt extrudates. These melt extrudates are finally milled with at least one erosion-enhancing agent and compressed into tablets.

In one embodiment, a mixture of an HIV protease inhibitor such as ritonavir and copovidone (and any other excipient(s) that may be present) may be blended via hot melt extrusion, followed by feeding the mixture into an extruder at a temperature typically ranging from 20° C. to 140° C., thus forming a hot melt extrudate. The extrudate may be further milled and compressed into tablets with the use of the erosion-enhancing agent (e.g., anhydrous dicalcium phosphate or its hydrate form), and any other excipient(s) that may be present in the composition. The compressed tablets thus formed may be film coated.

In some embodiments, the HIV protease is ritonavir. These embodiments are further described in the following subparagraphs.

1. A pharmaceutical composition containing a therapeutically effective amount of ritonavir, a pharmaceutically acceptable aqueous-soluble polymer, and an erosion-enhancing agent having a particle size distribution in the range of about 1 μm to about 350 μm, wherein the composition is free of surfactant.

2. The composition of subparagraph 1, wherein ritonavir is present in an amount of about 5 to about 30 wt %, based on the total weight of the composition.

3. The composition of subparagraph 1, wherein the therapeutically effective amount of ritonavir is about 25 mg to about 300 mg.

4. The composition of subparagraph 1, wherein the therapeutically effective amount of ritonavir contained therein is about 100 mg.

5. The composition of subparagraph 1, wherein the aqueous-soluble polymer has a glass transition temperature (Tg) of about 80° C. to about 180° C.

6. The composition of subparagraph 1, wherein the aqueous-soluble polymer is selected from the group consisting of homopolymers and copolymers of N-vinyl lactams, copolymers of N-vinyl pyrrolidone and vinyl acetate or vinyl propionate, cellulose esters, cellulose ethers, high molecular weight polyalkylene oxides, polyacrylates, polymethacrylates, polyacrylamides, vinyl acetate polymers, and polysaccharides.

7. The composition of subparagraph 1, wherein the aqueous-soluble polymer is a copolymer of N-vinyl pyrrolidone and vinyl acetate or vinyl propionate.

8. The composition of subparagraph 7, wherein the aqueous-soluble polymer is copovidone.

9. The composition of subparagraph 1, wherein the aqueous-soluble polymer is present in an amount of about 35 wt % to about 80 wt %, based on the total weight of the composition.

10. The composition of subparagraph 1, wherein the erosion-enhancing agent is selected from the group consisting of anhydrous dicalcium phosphate or its hydrate form, sodium chloride, potassium chloride, citric acid, tartaric acid, and succinic acid, and combinations of two or more thereof.

11. The composition of subparagraph 10, wherein the erosion-enhancing agent is anhydrous dicalcium phosphate or its hydrate form.

12. The composition of subparagraph 1, wherein the particle size distribution of the erosion-enhancing agent is about 10 μm to about 150 μm.

13. The composition of subparagraph 12, wherein the particle size distribution of the erosion-enhancing agent is about 150 μm.

14. The composition of subparagraph 12, wherein the particle size distribution of the erosion-enhancing agent is about 60 μm.

15. The composition of subparagraph 12, wherein the particle size distribution of the erosion-enhancing agent is about 12 μm.

16. The composition of subparagraph 1, wherein the erosion-enhancing agent is present in an amount of about 5 wt % to about 20 wt %, based on the total weight of the composition.

17. The composition of subparagraph 1, further comprising a pharmaceutically acceptable excipient.

18. The composition of subparagraph 17, wherein the excipient comprises a lubricant.

19. The composition of subparagraph 18, wherein the lubricant is selected from the group consisting of sodium stearyl fumarate, magnesium stearate, stearic acid, and glyceryl behenate, and combinations of two or more thereof.

20. The composition of subparagraph 17, wherein the excipient comprises a glidant.

21. The composition of subparagraph 20, wherein the glidant is selected from the group consisting of colloidal silica and calcium silicate, and a combination thereof.

22. The composition of subparagraph 1, which is in the form of a tablet.

23. The composition of subparagraph 1, which is in the form of a capsule.

24. The composition of subparagraph 22 or 23, which is coated.

25. The composition of subparagraph 24, which comprises a) about 100 mg ritonavir, b) copovidone, and c) anhydrous dicalcium phosphate or its hydrate form.

26. A method of making a pharmaceutical composition, comprising formulating a therapeutically effective amount of ritonavir, a pharmaceutically acceptable aqueous-soluble polymer, and an erosion-enhancing agent having a particle size distribution in the range of about 1 μm to about 350 μm, into the pharmaceutical composition, wherein the composition is free of surfactant.

27. The method of subparagraph 26, comprising subjecting ritonavir and the aqueous-soluble polymer to hot melt extrusion, thus forming an extrudate, milling the extrudate and the erosion-enhancing agent, and compressing the milled extrudate and erosion-enhancing agent into a tablet.

28. A method of treating a subject infected with HIV, comprising administering to said subject a pharmaceutical composition comprising a therapeutically effective amount of ritonavir, a pharmaceutically acceptable aqueous-soluble polymer, and an erosion-enhancing agent having a particle size distribution in the range of about 1 μm to about 350 μm, wherein the composition is free of surfactant.

29. The method of subparagraph 28, wherein the composition is in the form of a tablet or capsule.

The invention will now be described in terms of the following, nonlimiting working examples and figures.

EXAMPLES

Example 1

Formulations 1-9 described in Table 1 were prepared by mixing ritonavir, colloidal silica (e.g., Aerosil 200) and copovidone (KOLLIDON® VA 64) to make a blend for hot melt extrusion. The blend was fed into an extruder at a temperature ranging from 20° C. to 140° C. to form melt extrudates. The extrudates were further milled, and mixed with anhydrous dicalcium phosphate or EUDRAGIT® E PO (erosion-enhancing agents) and excipients such as colloidal silica and sodium stearyl fumarate, and compressed into tablets.

TABLE 1

Formulation Compositions for Ritonavir Tablets, 100 mg

| Ingredients | Formulations (mg/tablet) | | | | | | | | |
|---|---|---|---|---|---|---|---|---|---|
| | 1 | 2 | 3 | 4 | 5 | 6 | 7 | 8 | 9 |
| Extrusion | | | | | | | | | |
| Ritonavir | 100 | 100 | 100 | 100 | 100 | 100 | 100 | 100 | 100 |
| Copovidone | 500 | 565 | 500 | 500 | 500 | 500 | 500 | 500 | 500 |
| Colloidal Silica | 5 | 5 | 5 | 5 | 5 | 5 | 5 | 5 | 5 |
| Extra Granular | | | | | | | | | |
| Anhydrous Dicalcium Phosphate (D50~150 μm) | — | — | — | 85 | 150 | — | — | — | — |
| Anhydrous Dicalcium | 85 | 85 | 50 | — | — | — | 150 | — | 85 |

TABLE 1-continued

Formulation Compositions for Ritonavir Tablets, 100 mg

| Ingredients | 1 | 2 | 3 | 4 | 5 | 6 | 7 | 8 | 9 |
|---|---|---|---|---|---|---|---|---|---|
| Phosphate (D50~60 μm) | | | | | | | | | |
| Anhydrous Dicalcium Phosphate (D50~12 μm) | — | — | — | — | — | 85 | — | — | — |
| EUDRAGIT ® E PO | — | — | — | — | — | — | — | 85 | — |
| Colloidal Silica | 2.5 | 2.5 | 2.5 | 2.5 | 2.5 | 2.5 | 2.5 | 2.5 | 2.5 |
| Sodium Stearyl Fumarate | 2.5 | 2.5 | 2.5 | 2.5 | 2.5 | 2.5 | 2.5 | 2.5 | 2.5 |
| Film Coating | | | | | | | | | |
| OPADRY ® White | — | — | — | — | — | — | — | — | 20 |
| Total Tablet Weight | 695 | 760 | 660 | 695 | 760 | 660 | 760 | 695 | 715 |

Example 2

Inventive Formulations 1 and 2 were evaluated as to the effect of the absence of surfactants and the presence of the aqueous-soluble polymer on the dissolution profile of ritonavir using a discriminating dissolution profile. The instrumentation involved a USP type II apparatus, 75 RPM, and 900 mL of 5 mM 6.8 phosphate buffer. As shown in FIG. 1, the inventive formulations were amorphous and lacked crystallinity, thus confirming that the lack of surfactant, and the amount of the aqueous-soluble polymer present therein (see amounts of copovidone in Formulations 1 and 2), had no negative effect on the amorphous nature of the inventive formulations.

Example 3

Figure 2:
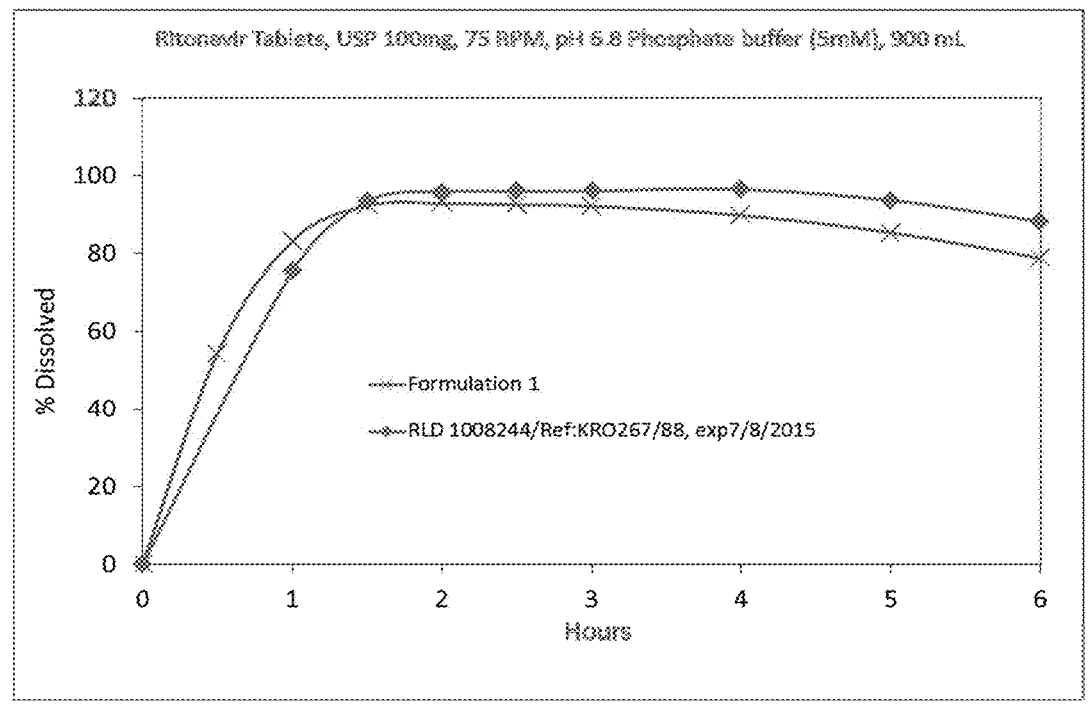
FIG. 2 compares inventive Formulation 1 with the reference product containing surfactant (NORVIR®) using discriminating dissolution, and shows that the inventive, surfactant-free formulation unexpectedly provided similar dissolution rate, recovery, and dissolution stability as compared with NORVIR®.

NORVIR® (which contains as inactive ingredients: butylated hydroxytoluene, ethanol, gelatin, iron oxide, oleic acid, polyoxyl 35 castor oil, and titanium dioxide) and Formulation 1 were compared from the standpoints of rate and extent of dissolution profile, using the apparatus and protocol described hereinabove. The experimentation was conducted with a paddle at 75 RPM, and using a 5 mM phosphate buffer, pH of 6.8. As shown in FIG. 2, the inventive formulation provided a comparable dissolution rate, along with comparable recovery and dissolution stability, as compared with NORVIR® (designated in FIG. 2 as RLD1008244/Ref:KR0267/88).

Example 4

Figure 3:
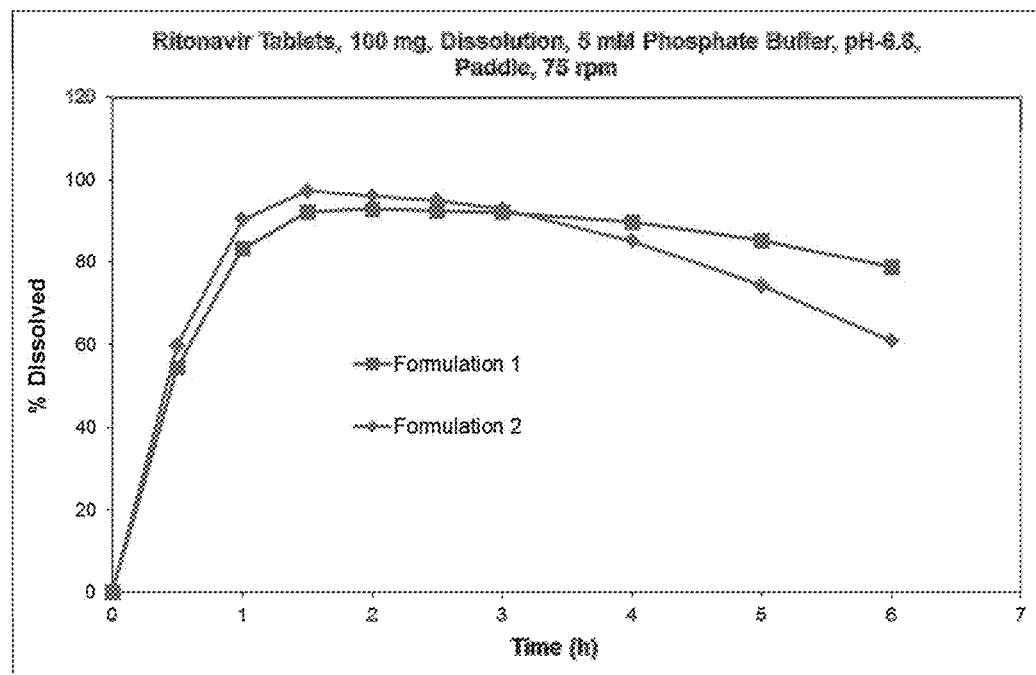
FIG. 3 shows the effect of an aqueous-soluble polymer of extrudate in Formulations 1 and 2 on dissolution of core tablets. The data show the effects of the amount/level of copovidone on the dissolution rate of Formulations 1 and 2, namely that the addition of an aqueous-soluble polymer beyond a certain point does not have a noticeable effect on the dissolution rate.

Formulations 1 and 2 were evaluated from the standpoint of the effect of the aqueous-soluble polymer on the dissolution of the tablets, using the apparatus and protocol described hereinabove. As shown in FIG. 3, the amount of the polymer (copovidone) after a certain point did not have any appreciable or noticeable effect on the dissolution rate.

Example 5

Figure 4:
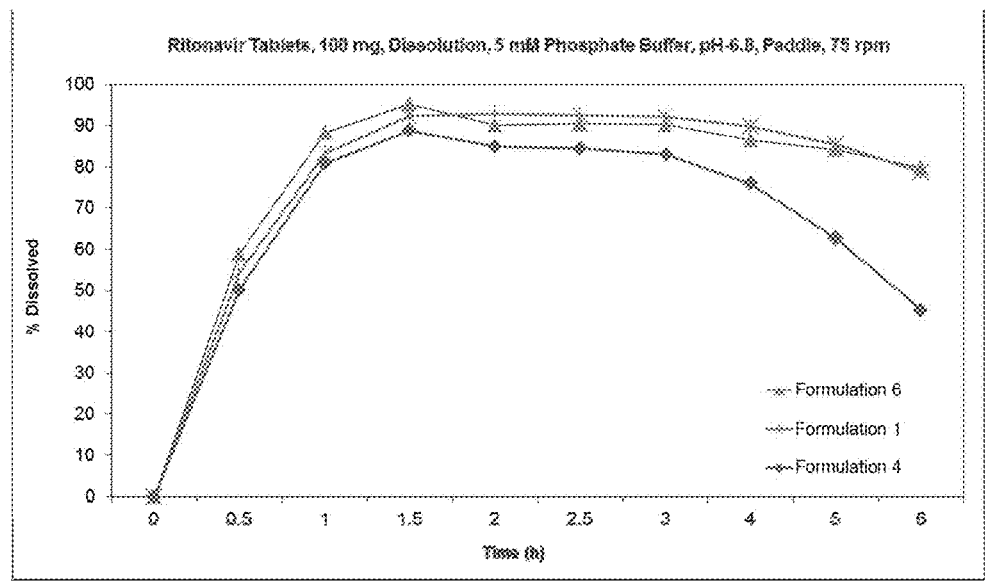
FIG. 4 shows the effect of the particle size distribution of the erosion-enhancing agent anhydrous dicalcium phosphate on the dissolution profile of inventive ritonavir tablets described herein as Formulations 1, 4, and 6. The data show that the particle size of anhydrous dicalcium phosphate (contained in Formulations 1, 4, and 6) impacts the recrystallization behavior of ritonavir in dissolution medium. The data also show that Formulations 1 and 6, with smaller average particle size of anhydrous dicalcium phosphate (DI-CAFOS® A 60 and DI-CAFOS® A12), exhibited better dissolution stability and less recrystallization compared to Formulation 4, which has a larger average particle size of anhydrous dicalcium phosphate (anhydrous EMCOMPRESS®).

Inventive Formulations 1, 4, and 6 were evaluated from the standpoint of the effect of the particle size distribution of the erosion-enhancing agent on the dissolution profile. The same apparatus and procedure as in the prior examples were used. The data illustrated in FIG. 4 show that the particle size of anhydrous dicalcium phosphate (contained in Formulations 1, 4, and 6) impacted the recrystallization behavior of ritonavir in dissolution medium. The data show that Formulations 1 and 6, with smaller average particle size of anhydrous dicalcium phosphate (DI-CAFOS® A 60 and DI-CAFOS® A12), exhibited better dissolution stability and less recrystallization compared to Formulation 4, which has a larger average particle size of anhydrous dicalcium phosphate (anhydrous EMCOMPRESS®).

Example 6

Figure 5:
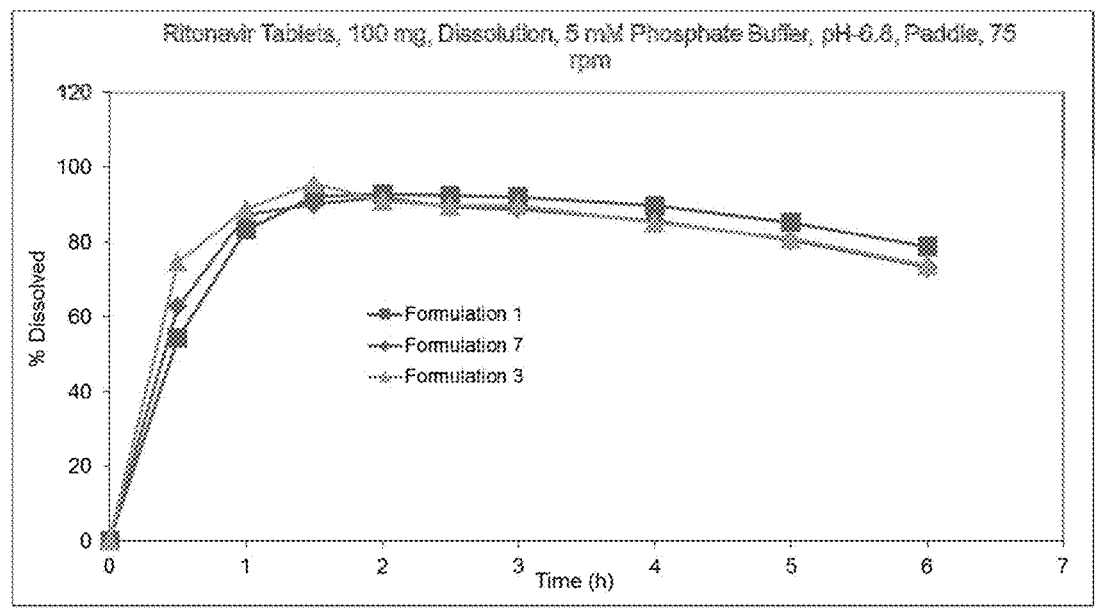
FIG. 5 shows the effect of the amount of the erosion-enhancing agent anhydrous dicalcium phosphate on dissolution of Formulations 1, 3, and 7. The data show that a finer average particle size of the erosion-enhancing agent (anhydrous dicalcium phosphate) helps maintain supersaturation for a longer duration of time regardless of the level or amount of erosion-enhancing agent, and that the formulations have minimal impact on dissolution of active drug.

Formulations 1, 3, and 7 were evaluated from the standpoint of the effect of the amount of an erosion-enhancing agent on tablet dissolution. The data graphically illustrated in FIG. 5 show that finer average particle size of the erosion-enhancing agent (which in these embodiments was anhydrous dicalcium phosphate (DI-CAFOS® A 60)) helps maintain super saturation for a longer duration of time regardless of the level or amount of the erosion-enhancing agent, and that the inventive formulations had minimal impact on the dissolution of ritonavir.

Example 7

Figure 6:
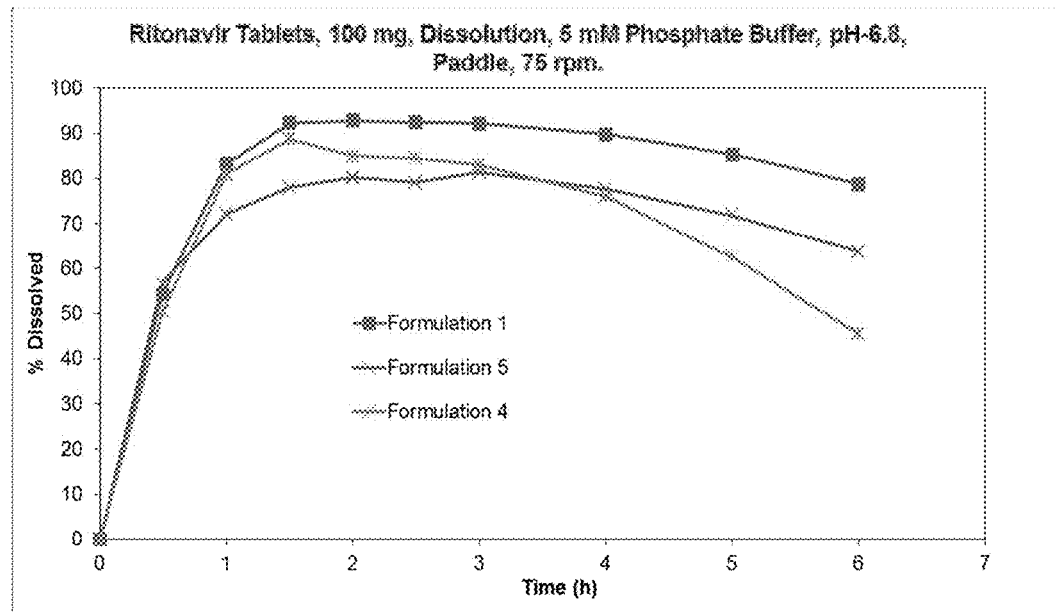
FIG. 6 shows the comparative dissolution for Formulations 1, 4, and 5. The data show that the erosion-enhancing agent anhydrous dicalcium phosphate with larger particle size requires a higher amount of the material (see Formulation 5) in order to slow the rate of recrystallization.

Formulations 1, 4, and 5 were evaluated from the standpoint of dissolution, using apparatus and protocols described hereinabove. As graphically presented in FIG. 6, the data show that an erosion-enhancing agent with a larger particle size (i.e., Formulation 5) requires a higher amount of the material in order to reduce the rate of recrystallization.

Example 8

Figure 7:
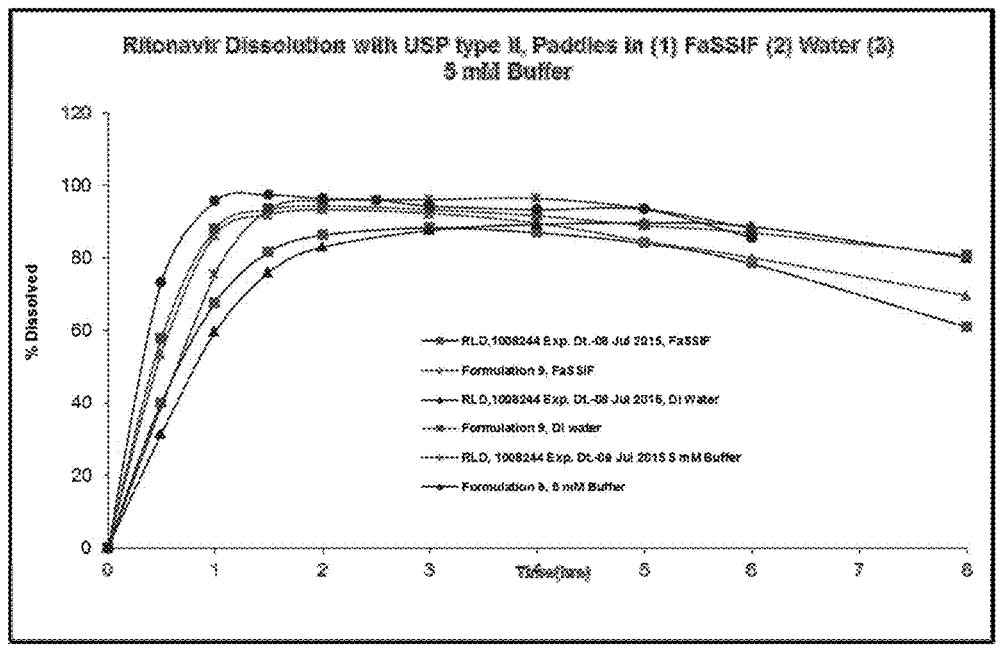
FIG. 7 shows the comparative dissolution for NORVIR® and the inventive, surfactant-free composition of Formulation 9 containing ritonavir, with USP type II, paddles in FaSSIF, water, and 5 mM buffer. The data show that the dissolution profile of the inventive, surfactant-free ritonavir formulation matches the dissolution profile of NORVIR® tablets.

Inventive Formulation 9 was compared to NORVIR® from the standpoint of dissolution, using apparatus and experimental protocols described hereinabove. The data, which are graphically shown in FIG. 7, show that the dissolution profile of inventive Formulation 9 matched the dissolution profile of the NORVIR® tablets.

Example 9

Formulation 9, an inventive, surfactant-free formulation, was tested against NORVIR® in a healthy volunteer bioequivalence study under a randomized, open label, balanced, three-sequence, two-treatment, three-period, reference replicate, crossover study in 48 normal, healthy, adult, male and female human subjects under fasting conditions. The pharmacokinetic data from the fasted bioequivalence study are shown in Table 2. The table shows the mean pharmacokinetic parameters for ritonavir comparing NORVIR® and Formulation 9 under fasted conditions.

TABLE 2

| PK PARAMETER | Formulation 9 (T) GEOMETRIC MEAN | NORVIR® (R) GEOMETRIC MEAN | % RATIO (T/R) | 90% CI LOWER LIMIT | 90% CI UPPER LIMIT | power |
|---|---|---|---|---|---|---|
| $AUC_{0-inf}$ ng * hr/mL | 9304.66 | 9419.5 | 98.7808 | 94.4922 | 103.2641 | 100 |
| $AUC_{0-t}$ ng * hr/mL | 8818.47 | 8931.52 | 98.7343 | 94.3407 | 103.3326 | 100 |
| Cmax ng/mL | 898.61 | 919.36 | 97.7431 | 92.5379 | 103.2412 | 100 |

Figure 8:
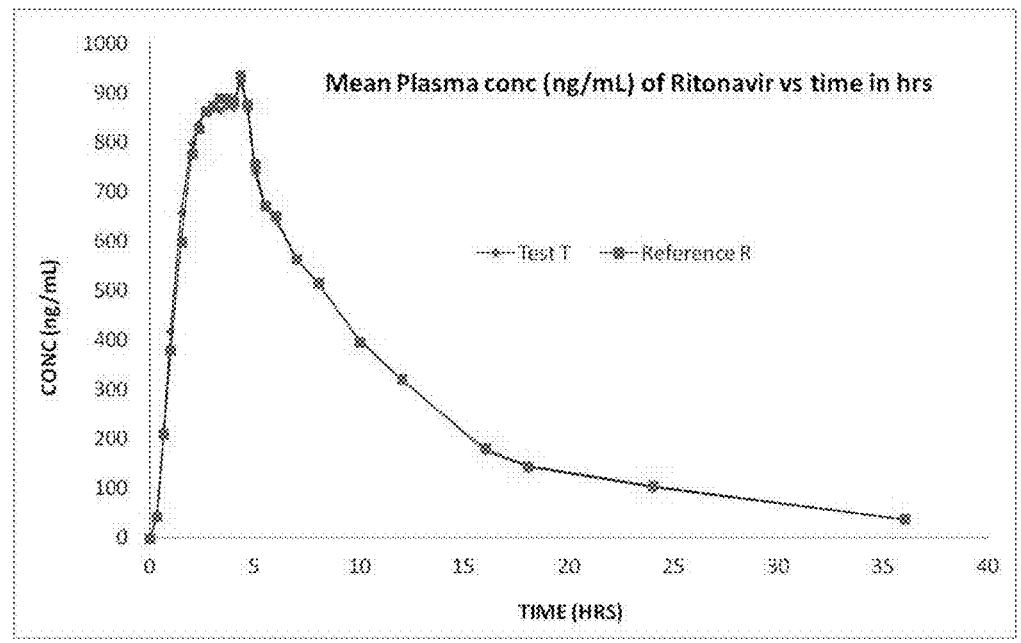
FIG. 8 shows mean plasma concentration of ritonavir after administration of Formulation 9 as compared with NORVIR® in a healthy volunteer bioequivalence study under fasting conditions. The data show that the two formulations were bioequivalent under fasted conditions.

As shown in Table 2, the ratios of the pharmacokinetic parameters—$AUC_{0-inf}$, $AUC_{0-t}$, and Cmax—of Formulation 9 (test) and NORVIR® (reference), and the 90% CI (confidence interval), are within the acceptance criteria known to one of skill in the art, i.e., 80-125%. These data are also graphically illustrated in FIG. 8. The data establish that Formulation 9 is bioequivalent with NORVIR® under fasted conditions.

Example 10

Formulation 9 was also tested against NORVIR® in a healthy volunteer bioequivalence study under a randomized, open label, balanced, two-treatment, two-period, two-sequence, single dose, crossover study in 56 normal, healthy, adult, male human subjects under fed conditions. The pharmacokinetic data from the fed bioequivalence study are shown in Table 3. The table shows the mean pharmacokinetic parameters for ritonavir comparing NORVIR® and Formulation 9 under fed conditions.

TABLE 3

| PK PARAMETER | Formulation 9 (T) GEOMETRIC MEAN | NORVIR® (R) GEOMETRIC MEAN | % RATIO (T/R) | 90% CI LOWER LIMIT | 90% CI UPPER LIMIT | power |
|---|---|---|---|---|---|---|
| $AUC_{0-inf}$ ng * hr/mL | 4665.77 | 5251.8 | 88.8413 | 84.6214 | 93.2717 | 100 |
| $AUC_{0-t}$ ng * hr/mL | 4361.95 | 4961.34 | 87.9187 | 83.426 | 92.6534 | 100 |
| Cmax ng/mL | 507.95 | 598.8 | 84.8293 | 80.0983 | 89.8397 | 100 |

Figure 9:
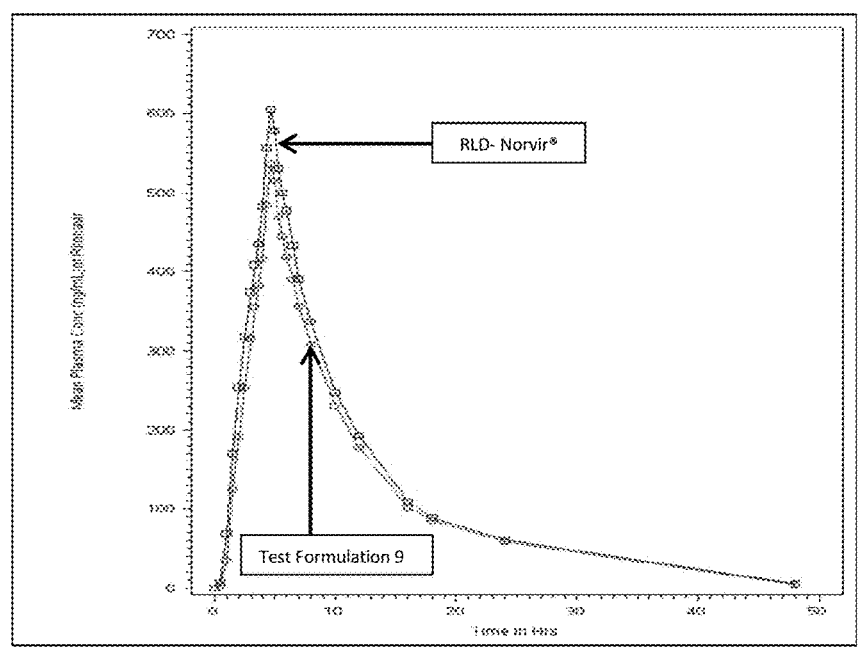
FIG. 9 shows mean plasma concentration of ritonavir after administration of Formulation 9 as compared with NORVIR® in a healthy volunteer bioequivalence study under fed conditions. The data show that the two formulations were bioequivalent under fed conditions.

As shown in Table 3, the ratios of the pharmacokinetic parameters—$AUC_{0-inf}$, $AUC_{0-t}$, and Cmax—of Formulation 9 (test) and NORVIR® (reference), and the 90% CI, are within the acceptance criteria known to one of skill in the art, i.e., 80-125%. The data are also graphically illustrated in FIG. 9. The data establish that Formulation 9 is bioequivalent with NORVIR® under fed conditions.

All patent and nonpatent publications cited in this specification are indicative of the level of skill of those skilled in the art to which this invention pertains. All these publications are hereby incorporated by reference herein to the same extent as if each individual publication was specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A pharmaceutical composition comprising: a melt extrudate and an extragranular component, wherein the melt extrudate comprises a solid dispersion comprising a therapeutically effective amount of amorphous ritonavir, and a pharmaceutically acceptable aqueous-soluble polymer, and the extragranular component comprises an erosion-enhancing agent having a particle size $D_{50}$ of about 60 µm or less, wherein the composition is free of surfactant, and wherein the therapeutically effective amount of amorphous ritonavir is about 100 mg.

2. The composition of claim 1, wherein the amorphous ritonavir is present in an amount of about 5 to about 30 wt %, based on the total weight of the composition.

3. The composition of claim 1, wherein the aqueous-soluble polymer has a glass transition temperature (Tg) of about 80° C. to about 180° C.

4. The composition of claim 1, wherein the aqueous-soluble polymer is selected from the group consisting of homopolymers and copolymers of N-vinyl lactams, copolymers of N-vinyl pyrrolidone and vinyl acetate or vinyl propionate, cellulose esters, cellulose ethers, high molecular weight polyalkylene oxides, polyacrylates, polymethacrylates, polyacrylamides, vinyl acetate polymers, and polysaccharides.

5. The composition of claim 1, wherein the aqueous-soluble polymer is a copolymer of N-vinyl pyrrolidone and vinyl acetate or vinyl propionate.

6. The composition of claim 5, wherein the aqueous-soluble polymer is copovidone.

7. The composition of claim 1, wherein the aqueous-soluble polymer is present in an amount of about 35 wt % to about 80 wt %, based on the total weight of the composition.

8. The composition of claim 1, wherein the erosion-enhancing agent is selected from the group consisting of anhydrous dicalcium phosphate or its hydrate form, sodium chloride, potassium chloride, citric acid, tartaric acid, and succinic acid, and combinations of two or more thereof.

9. The composition of claim 8, wherein the erosion-enhancing agent is anhydrous dicalcium phosphate or its hydrate form.

10. The composition of claim 1, wherein the erosion-enhancing agent has a particle size $D_{50}$ of about 12 µm or less.

11. The composition of claim 1, wherein the erosion-enhancing agent is present in an amount of about 5 wt % to about 20 wt %, based on the total weight of the composition.

12. The composition of claim 1, further comprising a pharmaceutically acceptable excipient.

13. The composition of claim 12, wherein the excipient comprises a lubricant.

14. The composition of claim 13, wherein the lubricant is selected from the group consisting of sodium stearyl fumarate, magnesium stearate, stearic acid, and glyceryl behenate, and combinations of two or more thereof.

15. The composition of claim 12, wherein the excipient comprises a glidant.

16. The composition of claim 15, wherein the glidant is selected from the group consisting of colloidal silica, calcium silicate, and a combination thereof.

17. The composition of claim 1, which is in the form of a tablet or a capsule.

18. The composition of claim 17, which is coated.

19. The composition of claim 17, which comprises a) copovidone, and b) anhydrous dicalcium phosphate or its hydrate form.

20. The composition of claim 1, wherein the ritonavir is in a stable amorphous form.

21. A method of making the pharmaceutical composition of claim 1, comprising formulating a therapeutically effective amount of ritonavir, a pharmaceutically acceptable aqueous-soluble polymer, and an erosion-enhancing agent having a particle size $D_{50}$ of about 60 µm or less, into the pharmaceutical composition, wherein the composition is free of surfactant, and wherein the therapeutically effective amount of ritonavir is about 100 mg.

22. The method of claim 21, comprising subjecting ritonavir and the aqueous-soluble polymer to hot melt extrusion, thus forming an extrudate, milling the extrudate and the erosion-enhancing agent, and compressing the milled extrudate and erosion-enhancing agent into a tablet.

23. A method of treating a subject infected with HIV, comprising administering to said subject the pharmaceutical composition of claim 1.

24. The method of claim 23, wherein the composition is in the form of a tablet or capsule.

25. A pharmaceutical composition comprising an intragranular component and an extragranular component, wherein the intragranular component comprises a therapeutically effective amount of amorphous ritonavir, and a pharmaceutically acceptable aqueous-soluble polymer, and the extragranular component comprises an erosion-enhancing agent having a particle size $D_{50}$ of about 60 µm or less, wherein the composition is free of surfactant, and wherein the therapeutically effective amount of amorphous ritonavir is about 100 mg.

26. The composition of claim 25, wherein the aqueous-soluble polymer has a glass transition temperature (Tg) of about 80° C. to about 180° C.

27. The composition of claim 25, wherein the aqueous-soluble polymer is selected from the group consisting of homopolymers and copolymers of N-vinyl lactams, copolymers of N-vinyl pyrrolidone and vinyl acetate or vinyl propionate, cellulose esters, cellulose ethers, high molecular weight polyalkylene oxides, polyacrylates, polymethacrylates, polyacrylamides, vinyl acetate polymers, and polysaccharides.

28. The composition of claim 25, wherein the ritonavir is in a stable amorphous form.

29. The composition of claim 25, wherein the extragranular component is free of a HIV protease inhibitor.

30. The composition of claim 25, wherein the extragranular component consists essentially of an erosion-enhancing agent having a particle size $D_{50}$ of about 60 µm or less, and at least one excipient.

31. The composition of claim 25, wherein the intragranular component comprises a solid dispersion comprising a therapeutically effective amount of amorphous ritonavir.

32. The composition of claim 25, wherein the erosion-enhancing agent has a particle size $D_{50}$ of about 12 µm or less.

33. A pharmaceutical composition comprising: a melt extrudate and an extragranular component, wherein the melt extrudate comprises an amorphous solid dispersion comprising about 100 mg of ritonavir in a stable amorphous form, and a pharmaceutically acceptable aqueous-soluble polymer selected from the group consisting of homopolymers and copolymers of N-vinyl lactams, copolymers of N-vinyl pyrrolidone and vinyl acetate or vinyl propionate, cellulose esters, cellulose ethers, high molecular weight polyalkylene oxides, polyacrylates, polymethacrylates, polyacrylamides, vinyl acetate polymers, and polysaccharides and mixtures thereof, present in an amount of about 35 wt % to about 80 wt %, based on the total weight of the composition, and the extragranular component comprises an erosion-enhancing agent selected from the group consisting of anhydrous dicalcium phosphate or its hydrate form, sodium chloride, potassium chloride, citric acid, tartaric acid, and succinic acid, and combinations of two or more thereof, present in an amount of about 5 wt % to about 20 wt %, based on the total weight of the composition and having a particle size $D_{50}$ of about 60 µm or less, wherein the composition is free of surfactant.

34. The composition of claim 33, wherein the erosion-enhancing agent has a particle size $D_{50}$ of about 12 µm or less.

35. A pharmaceutical composition comprising: a melt extrudate and an extragranular component, wherein the melt extrudate comprises a solid dispersion comprising a therapeutically effective amount of amorphous ritonavir, and a pharmaceutically acceptable aqueous-soluble polymer, and the extragranular component comprises an erosion-enhancing agent having a particle size $D_{50}$ of about 60 µm or less, wherein the composition is free of surfactant, the therapeutically effective amount of amorphous ritonavir is about 100 mg, and the composition maintains the ritonavir in a state of supersaturation when in contact with aqueous fluids in the gastrointestinal tract.

36. The composition of claim 35, wherein the erosion-enhancing agent has a particle size $D_{50}$ of about 12 µm or less.

* * * * *